United States Patent [19]

Spietschka et al.

[11] Patent Number: 4,588,814

[45] Date of Patent: May 13, 1986

[54] PROCESS FOR THE PREPARATION OF 3,4,9,10-PERYLENETETRACARBOXYLIC ACID DIIMIDE

[75] Inventors: Ernst Spietschka, Idstein/Taunus; Manfred Urban, Wiesbaden, both of Fed. Rep. of Germany

[73] Assignee: Hoechst Aktiengesellschaft, Fed. Rep. of Germany

[21] Appl. No.: 601,862

[22] Filed: Apr. 19, 1984

[30] Foreign Application Priority Data

Apr. 21, 1983 [DE] Fed. Rep. of Germany ....... 3314430
Dec. 17, 1983 [DE] Fed. Rep. of Germany ....... 3345810

[51] Int. Cl.$^4$ .................. C07D 221/14; C07D 471/06
[52] U.S. Cl. ..................................................... 546/37
[58] Field of Search ........................................ 546/37

[56] References Cited

FOREIGN PATENT DOCUMENTS 54806 6/1982 European Pat. Off. ............. 546/37
276357 7/1914 Fed. Rep. of Germany .
386057 12/1923 Fed. Rep. of Germany .
1202302 8/1970 United Kingdom .................. 546/37

OTHER PUBLICATIONS

Chem. Abstracts, 1948, 5892, pp. 2,1, 3.

Primary Examiner—George F. Lesmes
Assistant Examiner—S. A. Gibson
Attorney, Agent, or Firm—Connolly and Hutz

[57] ABSTRACT

Preparation of 3,4,9,10-perylenetetracarboxylic acid diimide by fusing naphthalene-1,8-dicarboxylic acid imide with potassium hydroxide and sodium acetate to give the alkali metal salt of the leuko compound of 3,4,9,10-perylenetetracarboxylic acid diimide, diluting the melt with water when the reaction has ended and oxidizing the leuko form to give the 3,4,9,10-perylenetetracarboxylic acid diimide, by a procedure which comprises (a) applying a vacuum of less than 100 mm Hg before the naphthalene-1,8-dicarboxylic acid imide is introduced into the potassium hydroxide/sodium acetate melt, heating the potassium hydroxide/sodium acetate mixture to 200°–300° C. and dehydrating it such that the melt is still stirrable at 200°–220° C., and then introducing the naphthalene-1,8-dicarboxylic acid imide or its sodium or potassium salt into the melt at 200°–220° C. under normal pressure and heating the mixture at 250°–300° C. in the absence of atmospheric oxygen, or (b) applying a vacuum of less than 100 mm Hg after the naphthalene-1,8-dicarboxylic acid imide or its sodium or potassium salt has been introduced into the potassium hydroxide/sodium acetate melt at 200°–220° C. under normal pressure, heating the mixture to 200°–250° C. and dehydrating it such that the melt is still stirrable at 200°–220° C., and then heating the melt at 250°–300° C. in the absence of atmospheric oxygen, or (c) introducing the sodium or potassium salt of naphthalene-1,8-dicarboxylic acid imide into the potassium hydroxide/sodium acetate melt at 200°–220° C. under normal pressure and heating the melt at 250°–300° C. in the absence of atmospheric oxygen.

1 Claim, No Drawings

PROCESS FOR THE PREPARATION OF 3,4,9,10-PERYLENETETRACARBOXYLIC ACID DIIMIDE

The invention relates to a process for the preparation of highly pure 3,4,9,10-perylenetetracarboxylic acid diimide in a high yield.

3,4,9,10-Perylenetetracarboxylic acid diimide and processes for its preparation are known. Thus, according to German Patent No. 386,057, 3,4,9,10-perylenetetracarboxylic acid diimide can be prepared by reacting 3,4,9,10-perylenetetracarboxylic acid dianhydride with ammonia. Although the product obtainable by this process is very pure, the process has the disadvantage that it is very expensive, because the 3,4,9,10-perylenetetracarboxylic acid dianhydride used as the reaction component is itself obtained from 3,4,9,10-perylenetetracarboxylic acid diimide by hydrolysis with concentrated sulfuric acid. This process is thus excluded as a solution to the industrial problem of preparing 3,4,9,10-perylenetetracarboxylic acid diimide from naphthalene derivatives which are readily accessible on a large industrial scale.

According to German Patent No. 276,357, 3,4,9,10-perylenetetracarboxylic acid diimide can be prepared by heating a mixture of naphthalene-1,8-dicarboxylic acid imide, potassium hydroxide and small amounts of water to temperatures of 280°–300° C. No information is given, however, on the yields and purity of the reaction product in the patent mentioned.

The 3,4,9,10-perylenetetracarboxylic acid diimide is obtained in an unsatisfactory purity and yield by the process described therein.

According to Chemical Abstracts 1948, 5892, a 3,4,9,10-perylenetetracarboxylic acid diimide is obtained in a yield of 75–81% of theory by fusing naphthalene-1,8-dicarboxylic acid imide with an alkali metal hydroxide with addition of water, and this product is said to be almost pure, according to spectroscopy. Following the information in Chemical Abstracts 1948, 5892 using ten times the batch size, it was not possible to confirm the assertion that a solution of 3,4,9,10-perylenetetracarboxylic acid diimide is formed, from which the diimide mentioned is obtained by acidification.

If sodium hydrokide is used as the fusing agent, a crude 3,4,9,10-perylenetetracarboxylic acid diimide is obtained in a yield of 46.1% of theory. In the usual purity determination method, a yield of only 57.8%, based on crude 3,4,9,10-perylenetetracarboxylic acid diimide, is achieved at the stage of the pure 3,4,9,10-perylenetetracarboxylic acid diimide. When potassium hydroxide is used, the crude yield is 81.2% of theory and the purity determination gives a value of 89.7%.

European Patent Application No. 0,054,806 describes a process for the preparation of 3,4,9,10-perylenetetracarboxylic acid diimide by fusion of naphthalene-1,8-dicarboxylic acid imide in a mixture of potassium hydroxide, sodium hydroxide and sodium acetate at temperatures of 190°–220° C. and subsequent oxidation, preferably in the melt. Yields of up to 93.4% are stated, and the purity of the product which can be obtained is described as high. However, no method of determination is mentioned.

It has now been found that 3,4,9,10-perylenetetracarboxylic acid diimide can be prepared with a high degree of purity and in a high yield by fusing naphthalene-1,8-dicarboxylic acid imide with potassium hydroxide and sodium acetate to give the alkali metal salt of the leuko compound of 3,4,9,10-perylenetetracarboxylic acid diimide, diluting the melt with water, when the reaction has ended, and oxidizing the leuko form to 3,4,9,10-perylenetetracarboxylic acid diimide, by a process which comprises (a) applying a vacuum of less than 100 mm Hg before the naphthalene-1,8-dicarboxylic acid imide is introduced into the potassium hydroxide/sodium acetate melt, heating the potassium hydroxide/sodium acetate mixture to 200°–300° C., preferably 250°–300° C., and hereby dehydrating this mixture such that the melt obtained is still stirrable at 200°–220° C. under industrial conditions, subsequently introducing the naphthalene-1,8-dicarboxylic acid imide or its sodium or potassium salt into the above melt at 200°–220° C. under normal pressure and heating this melt, in the absence of atmospheric oxygen, at 250°–300° C. until formation of the alkali metal salt of the leuko compound is complete, or (b) applying a vacuum of less than 100 mm Hg after the naphthalene-1,8-dicarboxylic acid imide or its sodium or potassium salt has been introduced into the potassium hydroxide/sodium acetate melt at 200°–220° C. under normal pressure, heating the mixture to 200°–250° C. and hereby dehydrating it such that the melt obtained is still stirrable at 200°–220° C. under industrial conditions, and subsequently heating the melt, in the absence of atmospheric oxygen, at 250°–300° C. until formation of the alkali metal salt of the leuko compound is complete, or (c) introducing the sodium or potassium salt of the naphthalene-1,8-dicarboxylic acid imide into the potassium hydroxide/sodium acetate melt at 200°–220° C. under normal pressure and heating the melt, in the absence of atmospheric oxygen, at 250°–300° C. until the formation of the alkali metal salt of the leuko compound is complete.

In detail, it is advantageous for the procedure of the process to use 3 to 10 parts by weight, preferably 3 to 6 parts by weight, of potassium hydroxide and 0.1 to 2 parts by weight, preferably 0.3 to 0.8 part by weight, of sodium acetate per part by weight of naphthalene-1,8-dicarboxylic acid imide or equivalent thereof in sodium or potassium salt.

The leuko compound of 3,4,9,10-perylenetetracarboxylic acid diimide intermediately obtained, according to the invention, by one of the routes (a ), (b) or (c) described above is oxidized in a manner which is known per se, for example by blowing in air (BIOS Final Report, 1484, page 21) or with peroxodisulfates, nitrates, chlorates, adducts of hydrogen peroxide and borates or hypochlorite solutions, in accordance with the statements of European Patent Application No. 0,054,806.

As regards the compounds of potassium hydroxide and sodium acetate used in the process according to the invention, the sodium acetate is used in anhydrous form, whilst the potassium hydroxide used is to be understood as meaning industrially available potassium hydroxide with a water content of 10–15%.

The naphthalene-1,8-dicarboxylic acid imide used according to the invention, or its sodium or potassium salt, is always to be understood as meaning the anhydrous compound, the sodium or potassium salt preferably being used (to avoid the formation of water in the melt by reaction of KOH with the naphthalene-1,8-dicarboxylic acid imide).

It is to be considered as surprising that the 3,4,9,10-perylenetetracarboxylic acid diimide can be obtained according to the invention, i.e. at relatively high reaction temperatures and/or with relatively long reaction times, since European Patent Application No. 0,054,806 reports that as short a reaction time as possible and as low a reaction temperature as possible lead to a high yield and high purity. According to the content determination, the 3,4,9,10-perylenetetracarboxylic acid diimide prepared by the process of the European Patent Application mentioned had a purity content of 81%, whilst the 3,4,9,10-perylenetetracarboxylic acid diimides prepared by the process according to the invention have purity contents of 90–95%.

The 3,4,9,10-perylenetetracarboxylic acid diimides obtained by the route according to the invention are outstandingly suitable for the preparation of 3,4,9,10-perylenetetracarboxylic acid diimide in pigment form as well as for alkylation products and as a starting substance for the preparation of 3,4,9,10-perylenetetracarboxylic acid dianhydride.

EXAMPLE 1

235 g of potassium hydroxide (85% pure) and 22.5 g of sodium acetate (anhydrous) are introduced into a stainless steel vessel with a stirrer. A vacuum (3 mm Hg) is then applied and the mixture is heated at 300° C. for 2 hours, during which 25 g of water escape. The mixture is then allowed to cool to 200° C. and 50 g of naphthalene-1,8-dicarboxylic acid imide (98.1% pure) are then introduced at this temperature in the course of 1 hour, whilst passing over nitrogen. The mixture is subsequently heated to 300° C. and is then stirred at this temperature for 6 hours. After cooling to 200° C., 300 ml of water are added dropwise, starting at this temperature, the melt thus diluted is then poured onto 1,500 ml of water, air is passed in at room temperature for 6 hours until oxidation of the leuko compound is complete, the precipitate is filtered off with suction and the residue on the filter is washed with water and then introduced into dilute hydrochloric acid. After the mixture has been stirred at 75° C. for 1 hour, the product is filtered off with suction, washed until neutral and dried at 80° C. 44.90 g of crude 3,4, 9,10-perylenetetracarboxylic acid diimide are obtained.

Determination of the pure content of 3,4,9,10-perylenetetracarboxylic acid diimide: 20 g of the crude 3,4,9,10-perylenetetracarboxylic acid diimide prepared as described above are introduced into 400 g of concentrated sulfuric acid. After the mixture has been warmed to 80° C. and the crude product mentioned has dissolved, 150 g of sulfuric acid (50% strength) are added dropwise in the course of 1 hour, during which the temperature may rise to 100° C. The mixture is then cooled to 25° C. and the precipitate is filtered off with suction, washed with 78% strength sulfuric acid until the runnings are clear and then washed until neutral and, finally, dried at 80° C. 18.48 g of pure 3,4,9,10-perylenetetracarboxylic acid diimide are obtained. The crude 3,4,9,10-perylenetetracarboxylic acid diimide obtained is thus 92.4% pure. This corresponds to a pure yield of 85.5% of theory, based on 100% pure naphthalene-1,8-dicarboxylic acid imide.

EXAMPLE 2

235 g of potassium hydroxide (90% pure) and 22.5 g of sodium acetate (anhydrous) are introduced into a stainless steel vessel with a stirrer. After the mixture has been heated up to 200° C., 62.5 g of the potassium salt of naphthalene-1,8-dicarboxylic acid imide (corresponding to 50 g of 100% pure naphthalene-1,8-dicarboxylic acid imide) are introduced in the course of 1 hour, whilst passing over nitrogen. After the mixture has been heated up to 300° C. and subsequently stirred at this temperature for 6 hours, it is allowed to cool to 200° C. and 300 ml of water are slowly added dropwise, starting at this temperature. The dilute melt is then poured onto 1,500 ml of water, air is passed in at room temperature for 6 hours until oxidation of the leuko compound is complete, the precipitate is filtered off with suction and washed with water, the residue on the filter is introduced into dilute hydrochloric acid, the mixture is subsequently stirred at 75° C. for 1 hour and the precipitate is filtered off with suction, washed until neutral and, finally, dried at 80° C.

46.22 g of 3,4,9,10-perylenetetracarboxylic acid diimide (95.0% pure) are obtained, corresponding to a pure yield of 88.7% of theory, based on 100% pure naphthalene-1,8-dicarboxylic acid imide. (The determination of the pure content of 3,4,9,10-perylenetetracarboxylic acid diimide is carried out by the method described in Example 1).

EXAMPLE 3

155 g of potassium hydroxide (90% pure) and 25 g of sodium acetate (anhydrous) are introduced into a stainless steel vessel with a stirrer. After the mixture has been heated up to 200° C., 60.6 g of the potassium salt of naphthalene-1,8-dicarboxylic acid imide (corresponding to 50 g of 100% pure naphthalene-1,8-dicarboxylic acid imide) are introduced at the above temperature in the course of 1 hour, whilst passing over nitrogen. A vacuum (40–50 mm Hg) is then applied and the mixture is then dehydrated at a temperature of up to 250° C. in the course of 2 hours, during which 6.9 g of water escape. The mixture is then heated to 260° C. under normal pressure and subsequently stirred at this temperature for 4 hours, whilst passing over nitrogen. After cooling to 200° C., 300 ml of water are added dropwise, starting at this temperature, the dilute melt is then poured onto 1,500 ml of water, air is passed in at room temperature for 6 hours until oxidation of the leuko compound is complete and the precipitate is filtered off with suction, washed with water and then introduced into dilute hydrochloric acid. After the mixture has been stirred at 75° C. for 1 hour, the product is filtered off with suction, washed until neutral and dried at 80° C.

45.5 g of 3,4,9,10-perylenetetracarboxylic acid diimide (91.0%) are obtained, which corresponds to a pure yield of 83.3% of theory, based on 100% pure naphthalene-1,8-dicarboxylic acid imide. (The determination of the pure content of 3,4,9,10-perylenetetracarboxylic acid diimide is carried out by the method described in Example 1).

EXAMPLE 4

235 g of potassium hydroxide (90% pure) and 22.5 g of sodium acetate (anhydrous) are introduced into a stainless steel vessel with a stirrer. A vacuum (40–50 mm Hg) is then applied and the mixture is heated at 300° C. for 2 hours, during which 12.4 g of water escape. The mixture is then allowed to cool to 200° C. and 62.5 g of the potassium salt of naphthalene-1,8-dicarboxylic acid imide (corresponding to 50 g of 100% pure naphthalene-1,8-dicarboxylic acid imide) are then introduced at this temperature in the course of 1 hour, whilst passing over nitrogen. Thereafter the mixture is heated to 300° C. and is subsequently stirred at this temperature for 6 hours. After cooling to 200° C., 300 ml of water are added dropwise, starting at this temperature, the dilute melt is then poured onto 1,500 ml of water, air is passed in at room temperature for 6 hours until oxidation is complete and the precipitate is filtered off with suction, washed with water and then introduced into dilute hydrochloric acid. After the mixture has been stirred at 75° C. for 1 hour, the product is filtered off with suction, washed until neutral and dried at 80° C.

48.0 g of 3,4,9,10-perylenetetracarboxylic acid diimide (95% pure) are obtained, which corresponds to a pure yield of 94.1% of theory, based on 100% pure naphthalene-1,8-dicarboxylic acid imide. (The determination of the pure content of 3,4,9,10-perylenetetracarboxylic acid diimide is carried out by the method described in Example 1).

EXAMPLE 5

235 g of potassium hydroxide (85% pure) and 22.5 g of sodium acetate (anhydrous) are introduced into a stainless steel vessel with a stirrer. A vacuum 3 mm Hg) is then applied and the mixture is heated at 300° C. for 2 hours, during which 24.8 g of water escape. The mixture is then allowed to cool to 200° C. and 62.5 g of the potassium salt of naphthalene-1,8-dicarboxylic acid imide (corresponding to 50 g of 100% pure naphthalene-1,8-dicarboxylic acid imide) are then introduced at this temperature in the course of 1 hour, whilst passing over nitrogen. The mixture is then heated to 250° C. and is subsequently stirred at this temperature for 6 hours. After cooling to 200° C., 300 ml of water are added dropwise, starting at this temperature, the dilute melt is poured onto 1,500 ml of water, the leuko compound formed is separated off from the mother liquor by filtration, the residue on the filter is stirred with five times the amount of water, air is then passed in until oxidation is complete, the pH is adjusted to 3 with dilute hydrochloric acid and the product is filtered off with suction, washed until neutral and dried at 80° C.

48.8 g of 3,4,9,10-perylenetetracarboxylic acid diimide (91.3% pure) are obtained, which corresponds to a pure yield of 90.0% of theory, based on 100% pure naphthalene-1,8-dicarboxylic acid imide. (The determination of the pure content of 3,4,9,10-perylenetetracarboxylic acid diimide is carried out by the method described in Example 1).

EXAMPLE 6

235 g of potassium hydroxide (85% pure) and 22.5 g of sodium acetate (anhydrous) are introduced into a stainless steel vessel with a stirrer. A vacuum (3 mm Hg) is then applied and the mixture is heated at 300° C. for 2 hours, during which 24.9 g of water escape. The mixture is then allowed to cool to 200° C. and 62.5 g of the potassium salt of naphthalene-1,8-dicarboxylic acid imide (corresponding to 50 g of 100% pure naphthalene-1,8-dicarboxylic acid imide) are then introduced at this temperature in the course of 1 hour, whilst passing over nitrogen. The mixture is then heated to 280° C. and subsequently stirred at this temperature for 2 hours. After cooling to 200° C., 300 ml of water are added dropwise, starting at this temperature, the dilute melt is poured onto 1,500 ml of water, air is passed in at room temperature for 6 hours until oxidation of the leuko compound is complete, the precipitate is filtered off with suction and the residue on the filter is washed with water and then introduced into dilute hydrochloric acid. After the mixture has been stirred at 75° C. for 1 hour, the product is filtered off with suction, washed until neutral and dried at 80° C.

47.9 g of 3,4,9,10-perylenetetracarboxylic acid diimide (91.6% pure) are obtained, which corresponds to a pure yield of 88.7% of theory, based on 100% pure naphthalene-1,8-dicarboxylic acid imide. (The determination of the pure content of 3,4,9,10-perylenetetracarboxylic acid diimide is carried out by the method described in Example 1).

EXAMPLE 7

235 g of potassium hydroxide (85% pure) and 22.5 g of sodium acetate (anhydrous) are introduced into a stainless steel vessel with a stirrer. A vacuum (3 mm Hg) is then applied and the mixture is heated at 300° C. for 2 hours, during which 26.3 g of water are removed. The mixture is then allowed to cool to 200° C. and 61.7 g of the sodium salt of naphthalene-1,8-dicarboxylic acid imide (corresponding to 50 g of 100% pure naphthalene-1,8-dicarboxylic acid imide) are then introduced at this temperature in the course of 1 hour, whilst passing over nitrogen. The mixture is then heated to 300° C. and is subsequently stirred at this temperature for 6 hours. After cooling to 200° C., 300 ml of water are added dropwise, starting at this temperature, the dilute melt is poured onto 1,500 ml of water, air is passed in at room temperature for 6 hours until oxidation of the leuko compound is complete, the precipitate is filtered off with suction and the residue on the filter is washed with water and then introduced into dilute hydrochloric acid. After the mixture has been subsequently stirred at 75° C. for 1 hour, the product is filtered off with suction, washed until neutral and dried at 80° C.

46.8 g of 3,4,9,10-perylenetetracarboxylic acid diimide (95.0% pure) are obtained, which corresponds to pure yield of 89.8% of theory, based on 100% pure naphthalene dicarboxylic acid imide. This determination of the pure content of 3,4,9,10-perylenetetracarboxylic acid diimide is carried out by the method described in Example 1).

We claim:

1. A process for the preparation of 3,4,9,10-perylenetetracarboxylic acid diimide with a high degree of purity and in a high yield in which yield the amount of 100% 3,4,9,10-perylene-tetracarboxylic acid diimide is comparatively high, by fusing naphthalane-1,8-dicarboxylic acid imide with potassium hydroxide and sodium acetate to give the alkali metal salt of the leuko compound of 3,4,9,10-perylenetetracarboxylic acid diimide, diluting the melt with water, when the reaction has ended, and oxidizing the leuko form to 3,4,9,10-perylenetetracarboxylic acid diimide, which comprises
(a) applying a vacuum of less than 100 mm Hg before the naphthalene-1,8-dicarboxylic acid imide is introduced into the potassium hydroxide/sodium acetate melt, heating the potassium hydroxide/sodium acetate mixture to 250°-300° C., and hereby dehydrating this mixture such that the melt obtained is still stirrable at 200°-220° C. under industrial conditions, subsequently introducing the naphthalene-1,8-dicarboxylic acid imide or its sodium or potassium salt into the above melt at 200°-220° C. under normal pressure and heating this melt, in the absence of atmospheric oxygen, at 250°-300° C. until formation of the alkali metal salt of the leuko compound is complete, or (b) applying a vacuum of less than 100 mm Hg after the naphthalene-1,8-dicarboxylic acid imide or its sodium or potassium salt has been introduced into the potassium hydroxide/sodium acetate melt at 200°–220° C. under normal pressure, heating the mixture to 200°–250° C. and hereby dehydrating it such that the melt obtained is still stirrable at 200°–220° C. under industrial conditions, and subsequently heating the melt, in the absence of atmospheric oxygen, at 250°–300° C. until formation of the alkali metal salt of the leuko compound is complete, or (c) introducing the sodium or potassium salt of the naphthalene-1,8-dicarboxylic acid imide into the potassium hydroxide/sodium acetate melt at 200°–220° C. under normal pressure and heating the melt, in the absence of atomspheric oxygen, at 250°–300° C. until the formation of the alkali metal salt of the leuko compound is complete.

* * * * *